United States Patent
Krishnareddy et al.

(10) Patent No.: US 10,422,886 B1
(45) Date of Patent: Sep. 24, 2019

(54) REAL-TIME LOCATION AWARE RADIATION SYSTEM AND METHOD FOR USE THEREOF

(71) Applicant: CLINITRAQ, Irvine, CA (US)

(72) Inventors: Divakar Krishnareddy, Huntington Beach, CA (US); Raghuram Bala, Santa Ana, CA (US); Hoang Tung, Garden Grove, CA (US)

(73) Assignee: CLINITRAQ, Irvine, CA (US)

( * ) Notice: Subject to any disclaimer, the term of this patent is extended or adjusted under 35 U.S.C. 154(b) by 0 days.

(21) Appl. No.: 15/817,001

(22) Filed: Nov. 17, 2017

Related U.S. Application Data

(60) Provisional application No. 62/423,653, filed on Nov. 17, 2016.

(51) Int. Cl.
   *G01T 1/02* (2006.01)
   *A61N 5/10* (2006.01)

(52) U.S. Cl.
   CPC ............ *G01T 1/026* (2013.01); *A61N 5/1071* (2013.01)

(58) Field of Classification Search
   CPC .............................. G01T 1/026; A61N 5/1071
   USPC .............................. 250/336.1, 370.07, 370.01
   See application file for complete search history.

(56) References Cited

U.S. PATENT DOCUMENTS

| | | | | |
|---|---|---|---|---|
| 5,179,281 A | * | 1/1993 | Tawil | G01T 1/11 250/337 |
| 6,765,214 B1 | * | 7/2004 | Kosslow | G01T 1/14 250/376 |
| 8,242,464 B1 | * | 8/2012 | Patel | G01T 1/04 250/472.1 |
| 8,803,089 B2 | * | 8/2014 | Walerow | G06F 19/34 250/336.1 |
| 2011/0159815 A1 | * | 6/2011 | Wu | H01Q 1/243 455/41.2 |
| 2013/0237811 A1 | * | 9/2013 | Mihailescu | A61B 5/064 600/424 |
| 2013/0320212 A1 | * | 12/2013 | Valentino | G01J 1/0488 250/336.1 |
| 2018/0196147 A1 | * | 7/2018 | Kang | G01T 1/20 |

* cited by examiner

*Primary Examiner* — David P Porta
*Assistant Examiner* — Blake C Riddick
(74) *Attorney, Agent, or Firm* — Rutan & Tucker, LLP

(57) ABSTRACT

A method for detecting radiation exposure by a smart radiation dosimeter (SRD) is described. The method comprises a step of activating a radiation sensor of the SRD by establishing a communicative coupling between the radiation and a dongle of the SRD. The method also comprises receiving, by the radiation sensor, personal identification information (PII) from the dongle, the PII identifying an individual holding the SRD. The method also comprises detecting, by the radiation sensor, a radiation level and recording, by the radiation sensor, the radiation level. The method also comprises generating, by the radiation sensor, one or more data packets that include the radiation level, the PII, a time stamp of when the radiation level was detected and location information pertaining to where the radiation level was detected; and transmitting the one or more data packets to a network device or cloud storage.

20 Claims, 4 Drawing Sheets

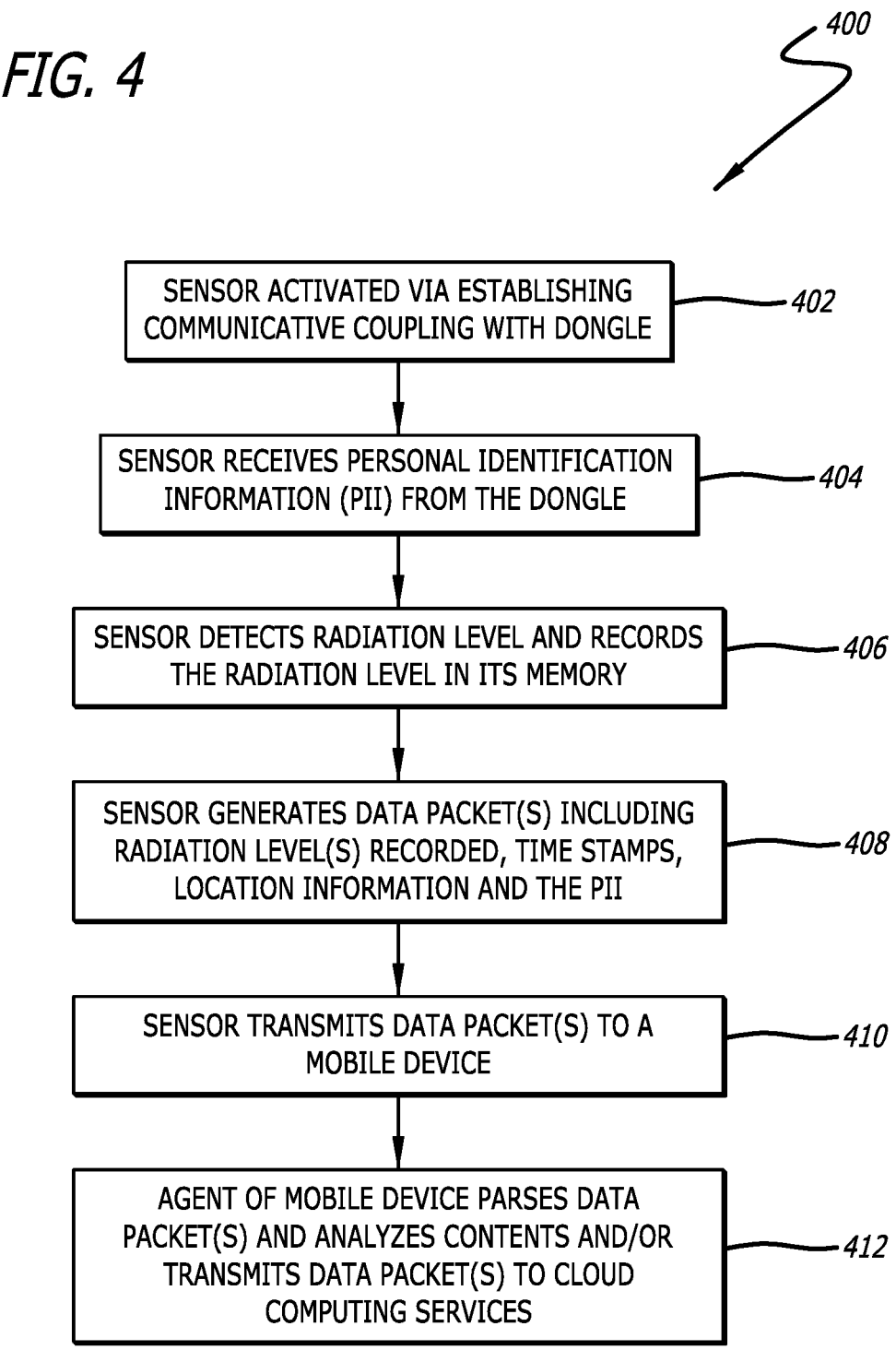

REAL-TIME LOCATION AWARE RADIATION SYSTEM AND METHOD FOR USE THEREOF

CROSS-REFERENCE TO RELATED APPLICATIONS

This application claims the benefit of priority to U.S. Provisional Application No. 62/423,653, filed Nov. 17, 2016, the entire contents of which are incorporated by reference herein.

FIELD

Embodiments of the disclosure relate to the field of sensor devices. More specifically, one embodiment of the disclosure relates to system and method utilizing a smart radiation dosimeter to detect radiation exposure over time.

GENERAL BACKGROUND

Modern medicine has utilized sensors for decades—thermometers, blood pressure monitors, urine analysis strips are all sensors in various forms. These sensors, when subjected to input, provide a reading that translates to a data point for a physician in his/her diagnosis of a patient. However, these sensors provide isolated readings.

The Internet of Things, or IoT, refers to the internetworking of smart, connected devices for the purpose of collecting and exchanging data. However, the field of medicine does not currently utilize smart IoT-enabled sensors to full potential. Additionally, conventional dosimeters include electronic personal dosimeters that provide continual monitoring and film badge dosimeters that are for a one-time use. However, continual readings, without more, fail to provide the necessary safety precautions for doctors or other healthcare facility employees routinely in the vicinity of radiation equipment. For example, a doctor may be constantly exposed to radiation levels just below a threshold that if exceeded would cause the doctor to be alerted; however, such constant exposure may be detrimental to the long-term health of the doctor yet the doctor would not be alerted of such. Similarly, film badge dosimeters merely provided a single use case and whether the use case is over a 24 hour period or a 30 day period, for example, no continuous monitoring is available. Therefore, as with the electronic dosimeter example provided above, the use of a film badge dosimeter without more fails to provide sufficient safety precautions.

Furthermore, conventional electronic personal dosimeters tend to be expensive, e.g., often exceeding a cost of $100 per electronic personal dosimeter. Thus, providing such for each employee often proves far too expensive for hospitals or healthcare facilities. As a result, some or all employees may not wear or carry a personal dosimeter and be unaware of their exposure to radiation.

Thus, an improved system and method for real-time detection and recordation of radiation exposure in a location-aware manner is needed.

BRIEF DESCRIPTION OF THE DRAWINGS

Embodiments of the disclosure are illustrated by way of example and not by way of limitation in the figures of the accompanying drawings, in which like references indicate similar elements and in which:

FIG. 4 is an exemplary embodiment of a flowchart illustrating operations of the real-time location aware radiation system 100 of FIG. 1.

DETAILED DESCRIPTION

I. Overview Summary

Figure 1:
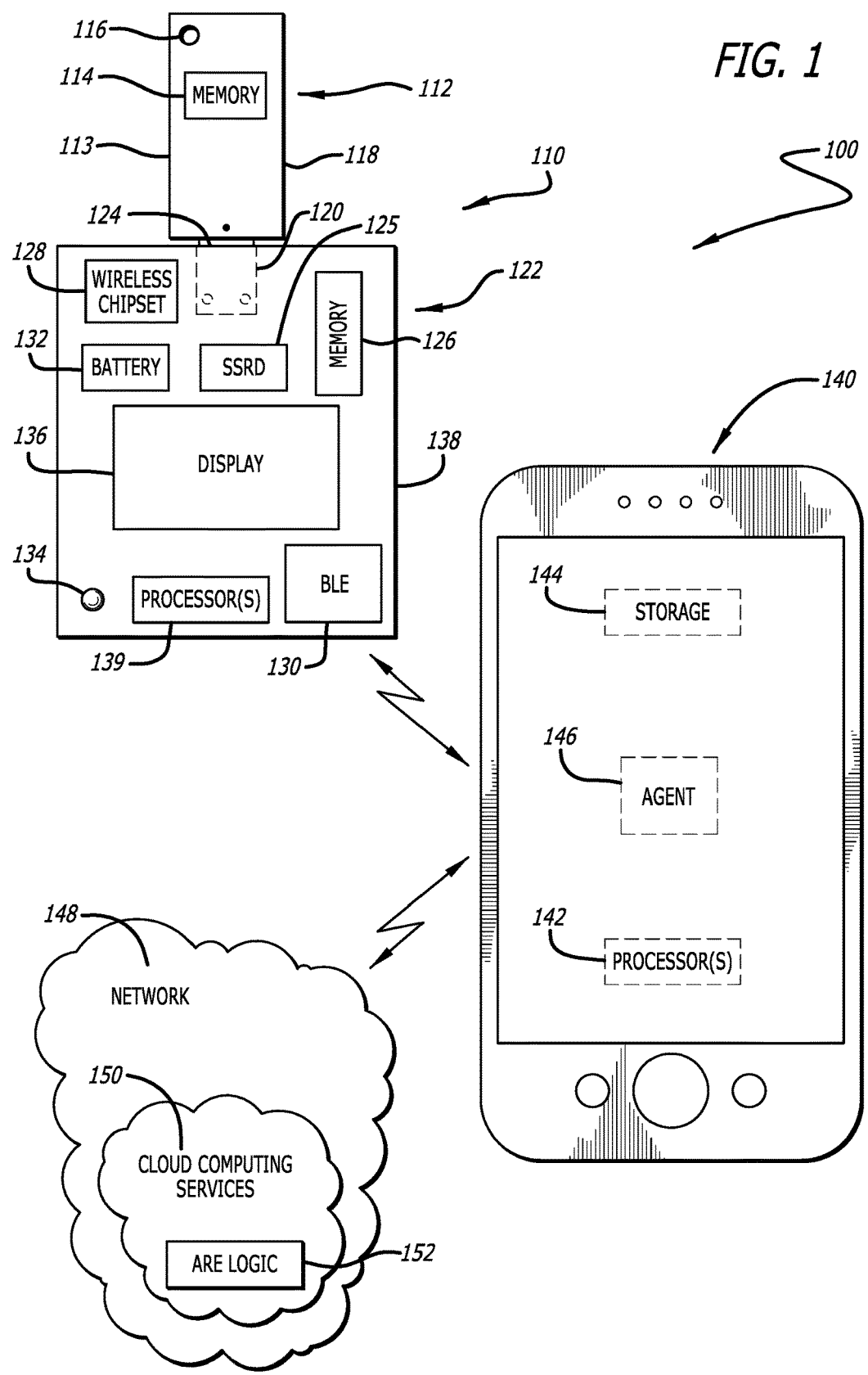
FIG. 1 is an exemplary block diagram of a smart radiation dosimeter (SRD) communicatively coupled to an electronic device.

Embodiments of a real-time location aware radiation system and method for use thereof are described. The real-time location aware radiation system provided is capable of utilizing multi-component smart radiation dosimeter to detect and track radiation exposure of one or particular individuals while, optionally, utilizing cloud computing services to determine patterns and levels of radiation exposure to the one or more individuals over time.

As current scenarios in which dosimeters are utilized in the medical field do not store information on the cloud, there is no ability to measure the cumulative exposure for each employee (e.g., wearer or carrier of a dosimeter) over a period of time. Thresholds and guidelines have been established within the medical industry that provide safety levels for a given individual over a predetermined time period, e.g. 100 mRads a month. In the invention of the disclosure, a dosage to which a particular individual has been exposed can be stored and monitored in the cloud enabling safety alerts or other notifications via an application installed on the individual's mobile device (alternative forms of alerts may include text messages and/or emails).

In addition to collecting radiation data from SRDs carried or worn by each employee, patterns may be determined and analyzed, e.g., via machine learning and predictive analytics. As a result, forecasts or predictions may be generated in a statistically sound manner using various algorithms to verify hypothesis pertaining to radiation exposure. In one example, when radiation levels in a given room within a hospital are seen to increase slightly over a period of time, such a pattern may indicate that the shielding material on a piece of radiation equipment within the room is poor, or that an employee who regularly frequents the room is not wearing sufficient protection. In the situation in which the shielding material of the piece of radiation equipment is poor, the hospital is notified so that a technician can replace or fix the shielding. In the situation in which the employee is not wearing sufficient protection, the hospital may wish to counsel the employee on safety measures or provide them better protective gear. In such an embodiment, each time the employee enters the room, he or she may have to record any protections he or she is wearing so that such can be correlated with the employee's radiation exposure within the room.

Many situations within the hospital-environment would benefit from the knowledge gained as a result of the real-time collection and aggregation of data from smart IoT-enabled sensors. As a first example, smart IoT-enabled sensors would enable the application of real-time rules processing and actuation in radiation dosimetry. Thus, upon carrying or wearing a particularized smart IoT-enabled sensor (e.g., a radiation dosimeter), doctors and hospital staff members would be able to monitor radiation exposure in real-time.

As a second example, radiation-guided oncology would benefit from the use of smart IoT-enabled devices in combination with machine learning techniques. Specifically, cancer treatments can be made significantly more effective by equipping patients with an IoT-enabled smart sensor (e.g., a radiation dosimeter) which performs real-time readings and stores the readings in the cloud for further analysis using, in one embodiment, machine learning techniques. For instance, analysis on the readings, biomarkers and health measurements of the patient may improve knowledge of the effectiveness of radiation-guided oncology enabling real-time adjustments of a patient's treatment.

II. Terminology

In the following description, certain terminology is used to describe various features of the invention. For example, each of the terms "logic" and "component" may be representative of hardware, firmware or software that is configured to perform one or more functions. As hardware, the term logic (or component) may include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the logic (or component) may include software such as one or more processes, one or more instances, Application Programming Interface (s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic (or component) may be stored in persistent storage.

Herein, a "communication" generally refers to related data that is received, transmitted, or exchanged within a communication session. The data may include a plurality of packets, where a "packet" broadly refers to a series of bits or bytes having a prescribed format. Alternatively, the data may include a collection of data that may take the form of an individual or a number of packets carrying related payloads, e.g., a single webpage received over a network.

The term "computerized" generally represents that any corresponding operations are conducted by hardware in combination with software and/or firmware.

The term "network device" may be construed as any electronic computing system with the capability of processing data and connecting to a network. Such a network may be a public network such as the Internet or a private network such as a wireless data telecommunication network, wide area network, a type of local area network (LAN), or a combination of networks. Examples of a network device may include, but are not limited or restricted to, an endpoint device (e.g., a laptop, a mobile phone, a tablet, a computer, etc.), a standalone appliance, a server, a router or other intermediary communication device, a firewall, etc.

The term "transmission medium" may be construed as a physical or logical communication path between two or more network devices or between components within a network device. For instance, as a physical communication path, wired and/or wireless interconnects in the form of electrical wiring, optical fiber, cable, bus trace, or a wireless channel using radio frequency (RF) or infrared (IR), may be used. A logical communication path may simply represent a communication path between two or more network devices or between components within a network device.

Finally, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

As this invention is susceptible to embodiments of many different forms, it is intended that the present disclosure is to be considered as an example of the principles of the invention and not intended to limit the invention to the specific embodiments shown and described.

III. Smart Radiation Dosimeter (SRD)

Referring now to FIG. 1, an exemplary block diagram of a smart radiation dosimeter (SRD) communicatively coupled to an electronic device is shown. Herein, a SRD 110 communicatively coupled to an electronic device, e.g., the mobile device 140, is shown as comprising the real-time location aware radiation system 100. Additionally, the mobile device 140 may be connected to a network 148, which may encompass or be connected to cloud computing services 150.

In particular, the SRD 110 is shown as including a dongle 112 and a sensor 122, which may be coupled together to establish a communicative coupling such that personal identification information (PII) may be transferred from the dongle 112 to the sensor 122. The dongle 112 is shown to include a memory 114, an optional keyring hole 116, an opening 118 and a coupler 120 (e.g., a standard-A USB plug) enclosed within a housing 113. As illustrated, the dongle 112 includes (i) a non-transitory storage medium (e.g., Flash storage) to store, at least, PII of the user (e.g., the SRD holder) also referred to herein as a "unique user identifier (UUID)," and (ii) a coupler 120 to connect to a coupling port of the sensor 122. The dongle 112 may take the form of a keychain or badge that can attach to the badge or set of keys of a doctor or hospital staff member. In alternative embodiments, the dongle 112 and the sensor 122 may communicatively couple is methods other than via USB and may include via other wired or wireless methods.

The sensor 122 is shown as including (i) a coupling port 124 (e.g., a USB port), (ii) a solid-state nuclear sensor, (iii) a memory 126, (iv) one or more communication interfaces 128-130, (v) a battery 132, (vi) a light (e.g., a light emitting diode (LED)) 134, (vii) a display 136 and (viii) one or more processors 139 enclosed within a housing 138. The housings 113 and 138 may comprised entirely or partially of a rigid material (e.g., hardened plastic, metal, glass, composite, or any combination thereof). The solid-state nuclear sensor 125 may detect radiation. For example, a semiconductor material such as silicon or germanium crystal may be used as detecting material within the solid-state nuclear sensor 125 in order to detect ionizing radiation particles. In one embodiment, the detection of ionizing radiation particles by the solid-state nuclear sensor 125 results in the generation of a pulse of current that may be recorded and analyzed to determine a level of detected radiation.

The memory 126 may be, for example, non-transitory storage medium such as Flash storage, and store logic (instructions such as firmware) that is processed by the one or more processors 139 to, inter alia, generate data packets as discussed below. The communication interfaces 128-130 may be, for example, a wireless chipset which may refer to a Wi-Fi chipset, wherein a chipset includes one or more integrated circuits, an ultra-wideband (UWB) radio transmitter/receiver (hereinafter, the term transmitter/receiver will be referred to as "transmitter"), a Bluetooth® transmitter, such as a Bluetooth Low Energy (BLE) transmitter and/or other chipsets/radio associated with other wireless technologies such as the Long-Term Evolution (LTE) standard or the 5G standard. In one embodiment, a UWB transmitter may enable the collection of location data and transmission of the location data, and the radiation data to cloud computing services 150 (as discussed below, radiation data may comprise radiation readings along with precise time, date and location information of the reading). Alternatively, or in addition, the BLE transmitter 130 may be used to communicatively couple the SRD 110 to the mobile device 140 and transmit the radiation data to the agent 144 installed and processing on the mobile device 140. In one embodiment, in which the SRD 110 does not include a UWB chipset, the mobile device 140 may transmit the radiation data and corresponding PII to cloud storage once it has been received from the SRD 110 via BLE connectivity. In yet other embodiments, the wireless chipset 128 may include technologies enabling alternative methods of transmitting the radiation data and corresponding PII to cloud storage, as discussed below. The sensor 122 may also include a battery 132, that may be charged when the sensor 122 is coupled to a power source via, e.g., the USB port 120, a secondary port 300 as seen in FIG. 3B, a Qi wireless charging station assuming the sensor 122 includes corresponding technology to receive power via the Qi wireless charging station (or other wireless charging technology).

The LED 134 may provide an indication of power remaining in the battery 132 for the SRD 110 and/or may be used to alert the SRD holder of a potentially unsafe situation in which a radiation exposure level is above an unsafe threshold or a cumulative level is above a predetermined threshold, as will be discussed below. Additionally, although the coupler 120 and the coupling port 124 are discussed herein as being a standard USB connector and communication port, the disclosure is not intended to be so limited. Instead, the coupling port 124 may be any communication means, such as, for example, a Lightning connector and corresponding communication port. In one exemplary embodiment, the dongle 112 may measure approximately a half of an inch thick, 3 inches wide, and 1 inch tall, while the sensor 122 may measure approximately a half of an inch thick, 3 inches wide and 3 inches tall. However, in other embodiments, the dimensions of either the dongle 112 and/or the sensor 122 may differ.

As mentioned above, conventional electronic personal dosimeters are expensive. However, the current disclosure provides an advantage over conventional electronic personal dosimeters by providing a SRD 100 comprised of two components: (1) the dongle 112, and (2) the sensor 122. The sensor 122 comprises the majority of the cost of the entire SRD 100. As a result, by providing a multi-component SRD 100, the invention of the disclosure enables a hospital or healthcare facility to purchase a plurality of sensors 122 based on the number of employees typically working at a single point in time and a plurality of dongles 112. Thus, each employee may be given a personal dongle 112 such that the PII of the personal dongle 112 is specific and unique to the particular employee. As each employee enters the hospital to begin his or her shift, he or she may pick up a sensor 122 (e.g., from an employee who worked the previous shift) and couple the sensor 122 to his or her personal dongle 112. Employees of a hospital may share sensors 122 and maintain their own personal dongles 112; therefore, the cost of providing SRDs to measure radiation of all employees is reduced as compared to conventional dosimeters.

The mobile device 140 may be communicatively coupled to the SRD 110 via its own BLE chipset, not shown. The mobile device 140 is shown to include a housing, a display, one or more processors 142, a non-transitory storage medium 144 and an agent (e.g., one or more logic modules) 146, which may be stored in the storage medium 144. In some embodiments, the mobile device 140 may receive the radiation data, location data and PII ("SRD data") from the SRD 110 and transmit the SRD data to the cloud computing services 150. The cloud computing services 150 may include logic, such as an analytics and rules engine (ARE) logic 152, as discussed below, and storage capabilities.

In one embodiment, a personal profile may be established for each employee, e.g., SRD holder, such that the data collected from the SRD associated with the employee is stored within the personal profile. In a second embodiment, in which the data collected by the SRD is transmitted to a mobile device that in turn transmits the data to cloud computing services 150, a Digital Twin is generated for the mobile device. Herein a Digital Twin may refers to a digital replica of the mobile device stored on the cloud. The benefits of a personal profile and/or a Digital Twin include: (i) storage of data for visualization and reporting; (ii) triggering of alerts and notifications based on analysis of the uploaded data; (iii) performance of machine learning operations on the uploaded data; (iv) creation of events in legacy enterprise systems e.g. Hospital Health Informatics systems based on the uploaded data; (v) triggering of events to the radiation device via "actuation" based on a logic modules and/or one or more predetermined rule set, which may result in, e.g., the triggering of a beeping sound when user's exposure levels exceed threshold levels and/or an automatic shut-off of certain radiation equipment; and (vi) sharing of data on blockchain for all ecosystem participants.

In one embodiment, in which the SRD 110 does not include a UWB chipset, the mobile device 140 may transmit the radiation data and corresponding PII to cloud storage once it has been received from the SRD 110 via BLE connectivity. As an alternative to using UWB to determine location, location of a particular detection by the sensor 122 may be determined according to, for example, use of location services associated with a mobile device communicatively coupled to the SRD 110, the use of beacons associated with wireless access points in order to utilize triangulation to approximate the location, and/or location/positioning technology associated with the LTE standard. For example, the 5G standard includes positioning, e.g., location aware, technology.

Figure 2A:
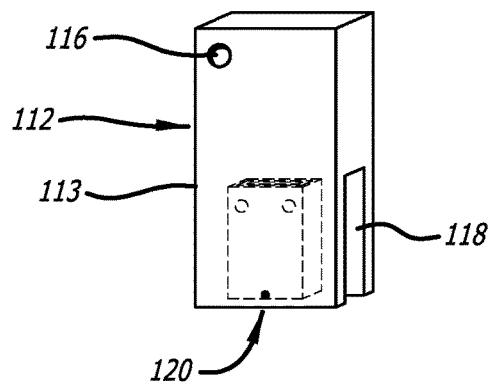
FIG. 2A is a first exemplary illustration of the dongle 112 of the SRD 110 of FIG. 1.
Figure 2B:
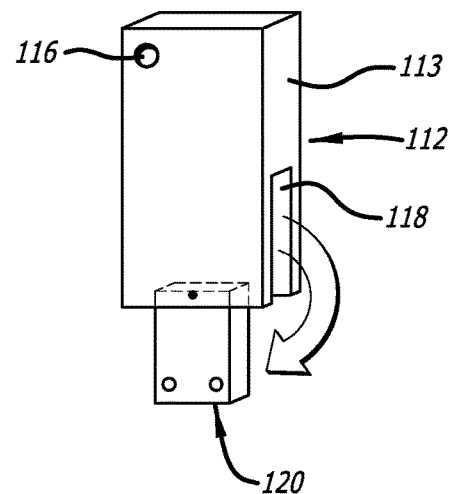
FIG. 2B is a second exemplary illustration of the dongle 112 of the SRD 110 of FIG. 1.

Referring to FIG. 2A, a first exemplary illustration of the dongle 112 of the SRD 110 of FIG. 1 is shown. FIG. 2A illustrates the USB connector 120 in a first position such that the connector is located within the housing 113 of the dongle 112 (e.g., hidden). The opening 118 is seen as enabling the USB connector 120 to rotate to a second position (as seen in FIG. 2B). Although not illustrated, a triggering device may be located on the dongle 112 in order to facilitate the rotation of the USB connector 120 between the first position and the second position. In one embodiment, the triggering device may be a mechanical component. Referring to FIG. 2B, a second exemplary illustration of the dongle 112 of the SRD 110 of FIG. 1 is shown. As mentioned previously, FIG. 2B illustrates the USB connector 120 in a second position, e.g., extending from the housing 113 of the dongle 112.

Figure 3A:
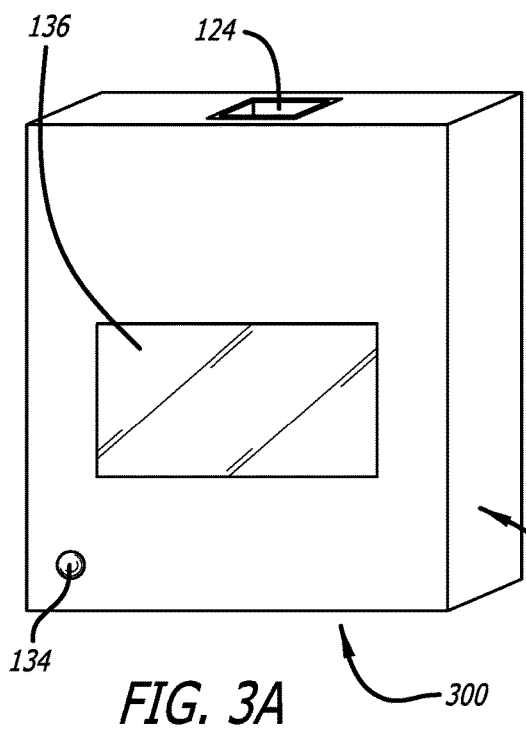
FIG. 3A is an exemplary illustration of the sensor 122 of the SRD 110 of FIG. 1.
Figure 3B:
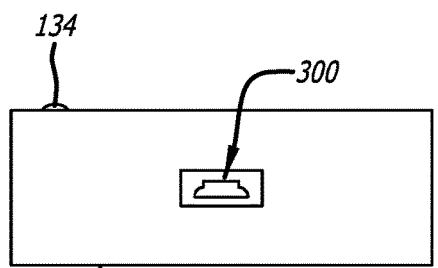
FIG. 3B is an exemplary illustration of a side, e.g., a bottom, of the sensor 122 of the SRD 110 of FIG. 1.

Referring to FIG. 3A, an exemplary illustration of the sensor 122 of the SRD 110 of FIG. 1 is shown. The exterior of the sensor 122 is shown to include the display 136, which may be, for example, a LED screen, a liquid crystal display (LCD) screen or an organic LED (OLED) screen, among other options as known in the art. The exterior of the sensor 122 is also seen to include the LED 134, the USB port 124 and an optional secondary port 300. The secondary port 300 may be, for example, a micro-USB port and dedicated to charging the sensor 122. Referring to FIG. 3B, an exemplary illustration of a side, e.g., a bottom, of the sensor 122 of the SRD 110 of FIG. 1 is shown. The secondary port 300 may be any of, inter alia, a micro-USB port, a standard USB port, a Lightning port, etc. Additionally, the secondary port 300 may be optional as the sensor 122 may, in some embodiments, be configured to allow for charging via the coupling port 124.

IV. Methodology of Real-Time Location Aware Radiation System

The use of smart IoT-enabled sensors, e.g., such as the SRD 100, may enable the application of real-time rules processing and actuation in radiation dosimetry. In particular, smart radiation dosimeter (SRD) such as SRD 100 may be utilized for collecting radiation exposure data at healthcare facilities. Unlike common radiation dosimeters that capture data on a film, over a 30 to 60 day window, the SRD 100 may comprise a solid-state electronic or nuclear dosimeter, which collects and disseminates radiation readings (x-rays, gamma and beta radiation, etc.). The SRD may also collect precise location and timestamp information in real-time via cloud connectivity. Utilizing IoT technology, sensors, such as the SRD 100, can now operate as part of a larger ecosystem of connected devices within the medical field. The sensory data captured by the SRD 100 may be transmitted through a network (e.g., Bluetooth Low Energy (BLE), Ultra-wideband (UWB), Wi-Fi, 4G, long-term evolution (LTE)) to cloud computing services. In some embodiments, as discussed above, the SRD 100 may utilize Wi-Fi technology and/or UWB technology to transmit sensory data (e.g., radiation data and/or SRD data) directly to cloud computing services. In alternative embodiments, the SRD 100 may communicatively couple to a mobile device 140, via e.g., BLE technology, to transmit sensory data to the mobile device, which in turn transmits the sensory data to cloud computing services.

One method of utilizing the SRD 100 includes the use of an analytics and rules engine, which may be represented by the agent 146 and/or logic within cloud computing services 150 ("analytics and rules engine (ARE) logic 152") as seen in FIG. 1. The agent 146 installed on the mobile device 146 may perform some or all of the operations and analyses as the ARE logic 152 processing within the cloud computing services 150. In some embodiments, the agent 146 may perform the same operations and analyses as the ARE logic 152 but on a subset of the data processed by the ARE logic 152. For instance, the ARE logic 152 may receive sensory data from a plurality of SRDs are performed analyses thereon, while the agent 146 performs the same analyses but only on data received from an SRD associated with a single dongle. Stated otherwise, the ARE logic 152 may perform analyses on data associated with a plurality of SRD holders (e.g., a plurality of healthcare facility employees) while the agent 146 may only perform the analyses on data received by a single SRD holder.

The analyses and operations performed by the agent 146 and/or the ARE logic 152 (hereinafter, reference will be made to the agent 146 but similar discussion pertains to the ARE logic 152 as well) may include an inspection of the incoming data packets from the SRD 100 in one or more ways. First, the agent 146 receives collected SRD data from the SD 100. The agent 146 may receive such in real-time or almost in real-time, e.g., at predetermined intervals, instead of waiting for a 30 or 60-day window as with conventional dosimeters. The agent 146 may then correlate and combine the recently received SRD data with previously received SRD data and present the combined SRD data to the SRD holder, e.g., via a graphic display on the mobile device. Alternatively, or in addition, the combined SRD data may be presented to the SRD holder via the LED or display of the sensor 122.

In particular, the agent 146 may determine whether a reading, e.g., a measurement, within the SRD data (captured radiation exposure information) is above a predetermined "safe" threshold. When a reading is above the safe threshold, the agent 146 may immediately inform the SRD holder about the unsafe reading and/or unsafe environment. In an alternative embodiment, edge computing algorithms may be employed by the SRD 100, which enable localized decision making without cloud connectivity in one embodiment of the method discussed above. These algorithms can be modified and adjusted with Over-The-Air (OTA) updates.

Second, an analysis of the cumulative exposure of an individual may be performed by the agent 146 over, for example, a rolling 30-day window by precise location and timestamp. Such an analysis significantly increases the safety of the SRD holder and reduces the liability of the healthcare facility.

In certain embodiments, correspondence with the stakeholders, the healthcare facility, and the SRD holder may be made through a mobile application. Additionally, when the exposure reaches unsafe levels, a notification may be generated by the agent 146, e.g., SMS, email, or mobile notification. Custom integration for actuation, e.g., the invocation of a remote command from the cloud to shutoff an x-ray device or other radiation provisioning equipment, or turning on a siren, has been contemplated as well.

As mentioned above, the radiation exposure of the healthcare facility employees (e.g., doctors and/or the hospital staff members) may be combined and subsequently patterns may be determined for each employee, or as a group, when in the vicinity of a particular machine, on a particular floor, in a particular department within the hospital, etc. For example, surgeons that perform surgery associated with kidney stones are often exposed to an excess amount of radiation during such surgeries. Thus, the SRD 100 worn by a surgeon performing surgery associated with kidney stones may monitor the radiation exposure of the surgeon during the surgery in real-time and alert the surgeon if the radiation exposure exceeds a predetermined threshold (e.g., an unsafe threshold). Additionally, such exposure to the surgeon may be tracked over the course of time, e.g., during several surgeries, so that patterns may be determined and exposure over the course of a sliding scale time period, e.g., over a rolling 30-day window, may be known. The information used to determine one or more patterns may also include the precise location of each reading by the SRD 100 and a corresponding timestamp.

As a second example of the method discussed above, the SRD 100 may be used by a doctor or medical device sales representative that works at multiple hospitals or healthcare facilities. For example, an SRD holder, such as a doctor, may wear the SRD 100 in the form of a badge or component that is attachable to the clothing of the SRD holder. Continuing the example, the SRD 100 and the readings captured therefrom need not be restricted to a specific hospital or singular location. Instead, the readings captured by the SRD 100 may be provided to (i) the hospital (e.g., via an access point), (ii) an electronic device (e.g., smart phone, tablet, etc.) for storage and/or (iii) cloud storage for association with a personal profile and storage thereon. More specifically, in one embodiment, the readings captured by the SRD 100 may be transmitted to an electronic device, e.g., a mobile phone 140, of the SRD holder. The mobile 140 phone may store the captured readings on non-transitory computer-readable medium located within the mobile phone 140. Alternatively, or in addition, the captured readings may be associated with a personal profile of the SRD holder and provided to cloud storage. Therefore, the SRD holder may be able to monitor radiation exposure when traveling between hospitals (or other locations at which the SRD holder may be exposed to radiation). It should be noted that the captured readings may include a reading of exposure of the SRD 100 to radiation, a location of the SRD 100 at the time of the reading, and a timestamp of the reading in association with PII of the SRD holder.

Thus, use of the SRD 100 enables a much faster reaction to cases of radiation overexposure unlike the current dosimetry devices. Additionally, use of the SRD 100 may be able to prevent radiation overexposure by alerting a SRD holder when radiation exposure is approaching an "unsafe" predetermined threshold and/or via actuation to shut off radiation equipment via automatic transmission of a signal from the agent 146 and/or the ARE logic 152.

Referring to FIG. 4, an exemplary embodiment of a flowchart illustrating operations of the real-time location aware radiation system 100 of FIG. 1 is shown. Each block illustrated in FIG. 4, with reference to FIG. 1, represents an operation performed in the method 400 of detecting radiation data and location data to track radiation exposure of the SRD 100. The method 400 begins when an a sensor is activated by the establishment of a coupling between a sensor 122 and the dongle 112 (block 402). Following activation of the sensor 122, the sensor receives personal identification information (PII) from the dongle 112, the PII identifying the employee holding the SRD 100 ("SRD holder") (block 404). At block 406, the sensor 122 detects radiation readings and records the radiation reading along with date, time and location information (referred to as "radiation data").

Following the recording of radiation data, the sensor 122 generates one or more data packets including the radiation information and the PII (collectively referred to as "SRD information") (block 408). Following the generation of the SRD one or more data packets, the sensor 122 transmits the one or more data packets to an electronic device of the SRD holder (block 410).

Upon the mobile device 140 receiving the one or more data packets, the agent 146 optionally parses the data packet and performs analyses on the SRD information and/or transmits the SRD information to the analytics and rules engine in the cloud computing services 150 (block 412).

Figure 5:
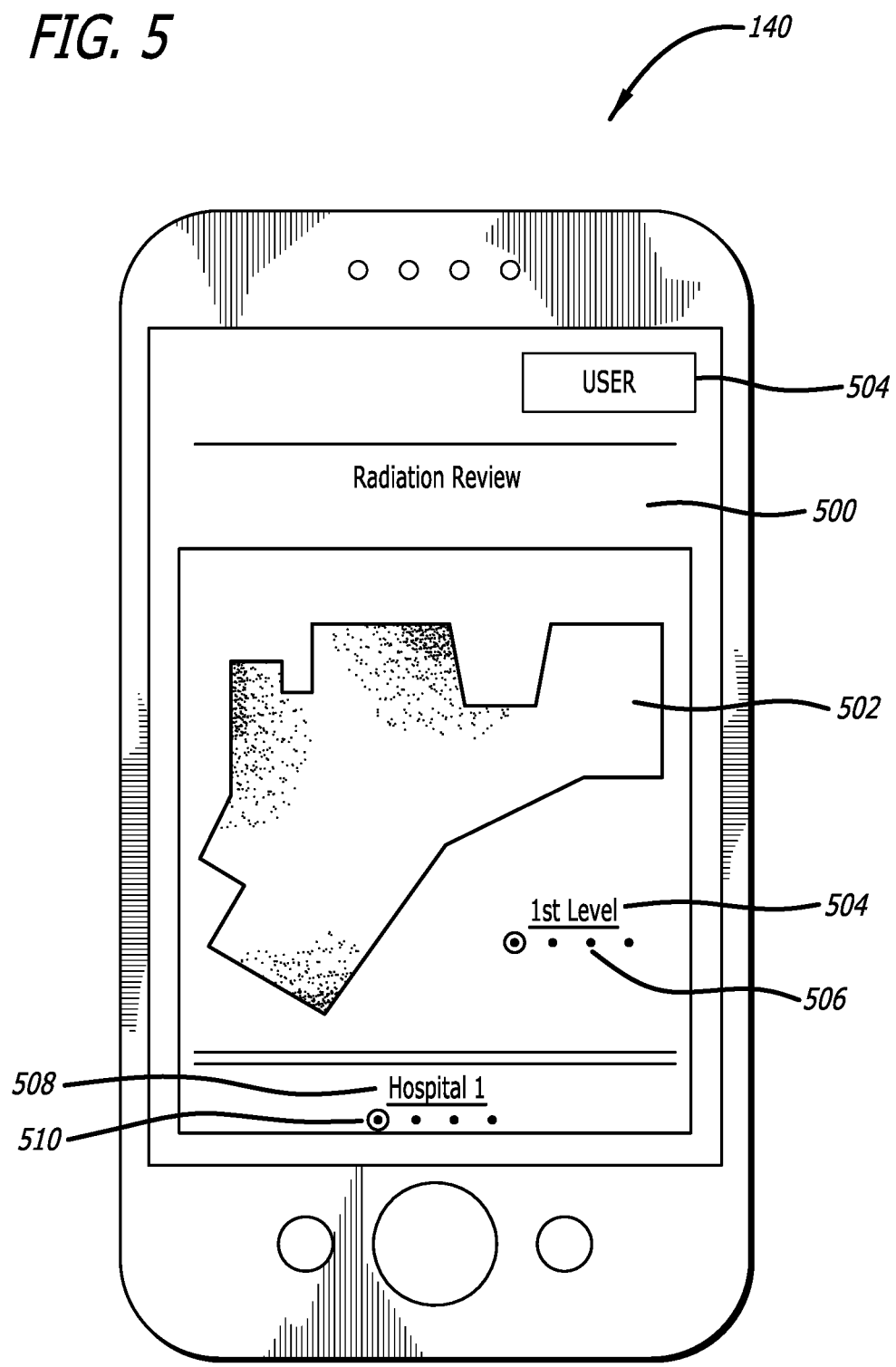
FIG. 5 is an exemplary block diagram of a display screen displayed by the mobile device 140 illustrating radiation exposure of one or more employees of a first hospital.

Referring to FIG. 5, an exemplary block diagram of a display screen displayed by the mobile device 140 illustrating radiation exposure of one or more employees of a first hospital is shown. The display screen 500 displayed on the mobile device 140 may be a display screen of a mobile application, e.g., the agent 146 as seen in FIG. 1. The display screen 500 may include a header portion 501 that indicates a particular user that is logged in. The display screen 500 may also include a graphic illustration displaying radiation exposure to one or more employees within a first hospital, e.g., a heat map 502. A graphic 504, e.g., text, may represent an indication of a level within a selected hospital or medical building to which the heat map belongs and a graphic 506, e.g., illustrated here as dots, may indicate a plurality of levels of the selected hospital or medical building (e.g., various floors) such that a swipe motion or some other form of input to the mobile device may change the selected level, and adjust the graphic 506 accordingly (e.g., place the circle around the corresponding dot). A graphic 508 may represent an indication of the selected hospital or medical building to which the heat map belongs and a graphic 510, e.g., dots, may indicate a plurality of hospitals or medical buildings such that a swipe motion or some other form of input to the mobile device may change the selected hospital or building displayed.

The display of the heat map 502 may change according to the selected hospital, medical building or level therein. For example, as a selected level is adjusted, the heat map 502 map change according to the floor plan of the selected and the radiation data collected for the selected level. In one embodiment, the heat map 502 represents radiation exposure of the particular individual indicated in the header 501. In some embodiments, the mobile application may enable various employees to log in to a single mobile device and/or the mobile application may enable one employee (or an administration for example) to access heat maps corresponding to radiation exposure of other employees. In yet another embodiment, the heat map 502 may illustrate the radiation exposure of all employees in a collective manner. In such an embodiment, all detected radiation data is transmitted to a cloud storage for analysis by the an analytics and rules engine processing within cloud computing services 150, for example. The analytics and rules engine may correlate all of the data and generate a heat map such as heat map 502 for each level of each hospital or medical building for which radiation data is received. In addition to a heat map, other graphics may be used to illustrate relative amounts of radiation exposure according to location within a hospital or medical building.

In yet another use case, radiation-guided oncology may benefit from the use of smart IoT-enabled devices, particularly a plurality of SRD devices, in combination with machine learning techniques. As is known, oncology is the study of cancer in three major areas: medical, surgical, and radiation. Medical oncology focuses on the treatment of cancer using chemotherapy. Surgical oncology involves the removal of cancerous tissues and performing biopsies for the detection of cancer. Radiation oncology focuses on treating cancer with radiation therapy.

Today, the primary use of dosimeters by healthcare workers is to measure their exposure levels to radiation. However, cancer treatments can be made significantly more effective by equipping patients with an IoT-enabled smart dosimeter such as the SRD 100, which performs real-time readings and stores the readings in the cloud for further analysis.

As discussed above, the SRD 100 may be equipped with a solid state nuclear sensor 125 as well as accompanying circuitry, collectively configured to detect and store radiation readings along with precise time, date and location information ("radiation data"). In some embodiments, the SRD 100 detects and stores radiation data in real-time, e.g., in cloud storage, or near real-time (e.g., at predetermined time intervals). The radiation data may then be analyzed using the ARE logic 152 and/or the agent 146. Collecting radiation data in real-time and analyzing at least a portion of all collected radiation data can improve cancer treatment protocols in a plurality of ways. First, errors in treatment procedures may be reduced. For example, cancer treatments need to expose patients to a certain amount of radiation at each session. If there are errors with the dosages provided to a patient, or if a patient is becoming overexposed to radiation, it could be injurious to the patient and pose a liability risk for the hospital. Using the real-time alerts of the ARE logic 152 and/or the agent 146, healthcare personnel may be notified of any dosage errors immediately as well as potential overexposure by a patient.

Second, radiation treatments may be guided based on data collected by a SRD 100 worn by a patient. For example, patients respond at different rates to radiation due to a number of factors such as age, gender, type of cancer, stage of cancer, diet, genetics, and more. Storing and analyzing the SRD radiation data via the ARE logic 152 in cloud computing services 150 and correlating the SRD radiation data to other data such as, a size of tumor, or cancer biomarkers (e.g., estimated glomerular filtration rate (eGFR), KRAS) from clinical readings to a time-series will create a personalized patient profile. This patient profile may aid in correlating the response rate of the patient to the radiation therapy via one or more machine learning algorithms can be employed to throttle radiation dosage. As the SRD 100 worn by the patient collects SRD data over time, the SRD data may be provided to the machine learning algorithms, which provide results as to the responsiveness of the patient to the radiation treatment. Such results of the responsiveness may enable adjustments to be made to the treatment procedure that may increase the efficacy of the radiation treatment. Additionally, the machine learning algorithms may automatically produce suggestions for such adjustments based on correlation of the current patient's profile and responsiveness to other similar patient profiles. For example, the methodology for guiding treatments through IoT and machine learning as discussed herein has a number of benefits, including using a corpus of data drawn from similar patients with a similar profile, machine learning algorithms can be trained to find the most optimal and, personalized treatment protocol. Additionally, the machine learning algorithms can also be further enhanced through a real-time feedback loop from a patient's response rate to a given dosage.

Therefore, the SRD 100 coupled with machine learning techniques provides real-time insights and can impact treatment regimens in a meaningful way. In particular, cancer treatments can be highly targeted based on biomarkers of a patient combined with exhaustive pattern matching capabilities of machine learning and the real-time response rates of patients.

In some embodiments, the data collected by the SRD 100 may be recorded on the blockchain. Blockchain technology offers an immutable, tamper-proof record of data and would be especially useful for consulting physicians who rove between hospitals and clinics each week. Currently any and all data collected at medical facilities is kept within an isolated "silo," e.g., the particular medical facility. However, such conventional data recorded does not provide a doctor who visits many facilities a true perspective of his or her exposure to radiation at each facility. In order to provide a true perspective, his or her cumulative exposure should be measured across the entire ecosystem (e.g., all medical facilities). By using blockchain, in a liability exposure/lawsuit scenario if the doctor were to get sick, the recordation via blockchain can indicate potential culpability based on for exposure levels for each medical facility with a date and time stamp. As a result, patterns may be generated over time to determine radiation exposure at each medical facility.

In the foregoing description, the invention is described with reference to specific exemplary embodiments thereof. It will, however, be evident that various modifications and changes may be made thereto without departing from the broader spirit and scope of the invention as set forth in the appended claims.

What is claimed is:

1. A method for detecting radiation exposure by a smart radiation dosimeter (SRD), the method comprising:
    activating a radiation sensor of the SRD by establishing a communicative coupling between the radiation sensor and a dongle of the SRD, wherein the radiation sensor comprises a first physical component and the dongle comprises a second physical component different than the first physical component;
    receiving, by the radiation sensor, personal identification information (PII) from the dongle, wherein the PII is stored on a memory of the dongle and identifies an individual associated with the SRD;
    detecting, by the radiation sensor, a radiation level;
    recording, by the radiation sensor, the radiation level;
    generating, by the radiation sensor, one or more data packets that include the radiation level, the PII, a time stamp of when the radiation level was detected and location information pertaining to where the radiation level was detected; and
    transmitting the one or more data packets to a network device or cloud storage.

2. The method of claim 1, wherein the communicative coupling is established by coupling a USB connector of the dongle with a USB port of the radiation sensor.

3. The method of claim 1, wherein the radiation level is recorded in non-transitory memory of the sensor.

4. The method of claim 1, further comprising:
    transmitting, by the network device, the one or more data packets to the cloud storage.

5. The method of claim 1, further comprising:
    determining, by an application processing on the network device, whether radiation exposure of the individual holding the SRD exceeds a first predetermined threshold based on an analysis of at least the one or more data packets.

6. The method of claim 5, wherein the first predetermined threshold pertains to a continuously rolling predetermined time period.

7. The method of claim 5, further comprising:
generating, by the application processing on the network device, an alert when the radiation exposure of the individual exceeds the first predetermined threshold.

8. The method of claim 7, wherein the alert includes a visual indication by a light emitting diode (LED) of the radiation sensor.

9. The method of claim 1, further comprising:
determining, by an application processing in a cloud computing environment and accessing at least the one or more data packets, whether radiation exposure of the individual holding the SRD exceeds a first predetermined threshold based on an analysis of at least the one or more data packets.

10. The method of claim 9, wherein the first predetermined threshold pertains to continuously rolling predetermined time period.

11. An apparatus for detecting radiation exposure, the apparatus comprising:
a dongle including a first non-transitory storage medium and a connector, the first non-transitory storage medium and the connector located within a housing of the dongle, wherein the first non-transitory storage medium stores personal identification information (PII) of an individual associated with the dongle; and
a detection device including (i) a communication port to receive the connector of the dongle, (ii) a radiation sensor, (iii) a second non-transitory storage medium, (iv) a wireless chipset, (v) one or more processors, and (vi) a battery, wherein the detection device comprises a first physical component and the dongle comprises a second physical component different than the first physical component.

12. The apparatus of claim 11, wherein the radiation sensor is a solid-state nuclear sensor.

13. The apparatus of claim 11, wherein the radiation sensor is configured to detect a radiation level, wherein the radiation level is recorded in the second non-transitory storage medium.

14. The apparatus of claim 13, further comprising:
logic stored in the second non-transitory storage medium, the logic was executed by the one or more processors, configured to (i) generate one or more data packets including the recorded radiation level and the PII, and (ii) cause transmission of the one or more data packets to a mobile device via the wireless chipset.

15. The apparatus of claim 11, wherein the wireless chipset is a Wi-Fi chip.

16. A system for detecting radiation exposure, the system comprising:
a smart radiation dosimeter (SRD) including
a dongle including a first non-transitory storage medium and a connector, the first storage medium and the connector located within a housing of the dongle, and wherein the first storage medium stores personal identification information (PII) of an individual associated with the dongle, and
a detection device including (i) a communication port to receive the connector of the dongle, (ii) a radiation sensor, (iii) a second storage medium, (iv) a wireless chipset, (v) a first set of one or more processors, and (vi) a battery, wherein the detection device comprises a first physical component and the dongle comprises a second physical component different than the first physical component,
wherein the detection device is configured to (a) detect a radiation level, (b) record the radiation level, (c) generate one or more data packets that include the radiation level, the PII, a time stamp of when the radiation level was detected and location information pertaining to where the radiation level was detected, and (d) transmit the one or more data packets to a network device or cloud storage; and
a non-transitory computer readable medium having stored thereon instructions that, when executed by a second set of one or more processors, causes execution of operations including
receiving the one or more data packets,
determining whether radiation exposure of an individual associated with the SRD exceeds a first predetermined threshold based on an analysis of at least the one or more data packets, and
generate an alert when the radiation exposure of the individual exceeds the first predetermined threshold.

17. The system of claim 16, wherein the non-transitory computer readable medium is located within the network device and the instructions stored on the non-transitory computer readable medium pertain to a mobile application.

18. The system of claim 16, wherein the non-transitory computer readable medium is located in a cloud computing environment and the instructions stored on the non-transitory computer readable medium pertain to logic processed in the cloud computing environment.

19. The system of claim 16, wherein the radiation sensor is a solid-state nuclear sensor.

20. The system of claim 16, wherein the wireless chipset is a Wi-Fi chip.

* * * * *